US009983201B2

(12) United States Patent
Aoki

(10) Patent No.: US 9,983,201 B2
(45) Date of Patent: May 29, 2018

(54) MICROCHIP SOLUTION SENDING SYSTEM

(71) Applicant: Youichi Aoki, Hachioji (JP)

(72) Inventor: Youichi Aoki, Hachioji (JP)

(73) Assignee: KONICA MINOLTA HOLDINGS, INC., Tokyo (JP)

(*) Notice: Subject to any disclaimer, the term of this patent is extended or adjusted under 35 U.S.C. 154(b) by 409 days.

(21) Appl. No.: 13/775,831

(22) Filed: Feb. 25, 2013

(65) Prior Publication Data
US 2013/0171739 A1 Jul. 4, 2013

Related U.S. Application Data

(62) Division of application No. 13/153,868, filed on Jun. 6, 2011.

(30) Foreign Application Priority Data

Jun. 9, 2010 (JP) ................... 2010-131970

(51) Int. Cl.
G01N 33/53 (2006.01)
G01N 33/543 (2006.01)
(Continued)

(52) U.S. Cl.
CPC ...... G01N 33/5306 (2013.01); B01F 11/0071 (2013.01); B01F 13/0059 (2013.01);
(Continued)

(58) Field of Classification Search
CPC ............... B01L 3/5027; B01L 9/527; B01L 2300/0636; B01L 2300/0819;
(Continued)

(56) References Cited

U.S. PATENT DOCUMENTS 5,313,264 A * 5/1994 Ivarsson et al. ................ 356/73
2003/0165953 A1 9/2003 Karube et al.
(Continued)

FOREIGN PATENT DOCUMENTS

JP 11-332595 A 12/1999
JP 2004-163259 A 6/2004
(Continued)

OTHER PUBLICATIONS

Notification of Reason for Rejection for Japanese Application No. 2011-123431, drafted Feb. 26, 2014 with English translation.
(Continued)

Primary Examiner — Dennis White
Assistant Examiner — Bryan Kilpatrick
(74) Attorney, Agent, or Firm — Cantor Colburn LLP

(57) ABSTRACT

[Technical Problem]
It is an object to provide a microchip solution sending system that is provided with the high reaction efficiency and the high detection accuracy.
[Solution of Problem]
A microchip solution sending system comprises a fine flow passage that is provided with a reaction field to which an antibody that reacts with a specific antigen is fixed and a solution sending pump that is configured to send a specimen material solution that includes the specific antigen, wherein a specimen material solution passes through a reaction field of a fine flow passage in a repetitive manner in the case in which the solution sending pump sends the specimen material solution, and a flow rate of a specimen material solution that is sent by the solution sending pump is in the range of 1,000 μl/min to 50,000 μl/min.

14 Claims, 10 Drawing Sheets

(51) Int. Cl.
*B01F 11/00* (2006.01)
*B01F 13/00* (2006.01)
*B01L 3/00* (2006.01)
*B01L 9/00* (2006.01)

(52) U.S. Cl.
CPC ............ *B01L 3/50273* (2013.01); *B01L 9/527* (2013.01); *G01N 33/54366* (2013.01); *B01L 2300/0654* (2013.01); *B01L 2400/0478* (2013.01)

(58) Field of Classification Search
CPC ...... G01N 21/01; G01N 21/05; G01N 21/658; B01F 15/00214; B81B 2201/051
USPC ......... 422/68.1, 82.05, 417; 436/501; 435/3, 435/283.1, 287.2
See application file for complete search history.

(56) References Cited

U.S. PATENT DOCUMENTS

2004/0028559 A1  2/2004  Schuck
2005/0272144 A1* 12/2005 Sando et al. ................ 435/287.2
2009/0128822 A1*  5/2009  Yamamichi .......... G01N 21/554
356/445

FOREIGN PATENT DOCUMENTS

| JP | 2005-134372 A | 5/2005 |
| JP | 2006-90985 A | 4/2006 |
| JP | 2006-242912 A | 9/2006 |

OTHER PUBLICATIONS

Extended European Search Report for Application No./Patent No. 11166648.3-2404 dated Aug. 2, 2011.
Sjolander S., et al., "Integrated Fluid Handling System for Biomolecular Interaction Analysis", Analytical Chemistry, American Chemical Society, US, vol. 63, No. 29, Oct. 15, 1991, pp. 2338-2345.
Yu F., et al., "Surface Plasmon Field-Enhanced Fluorescence Spectroscopy Studies of the Interaction between an Antibody and its Surface-Coupled Antigen", Analytical Chemistry Jun. 1, 2003 American Chemical Society US, vol. 75, No. 11, Jun. 1, 2003, pp. 2610-2617.

* cited by examiner

[Fig. 1]
(a)
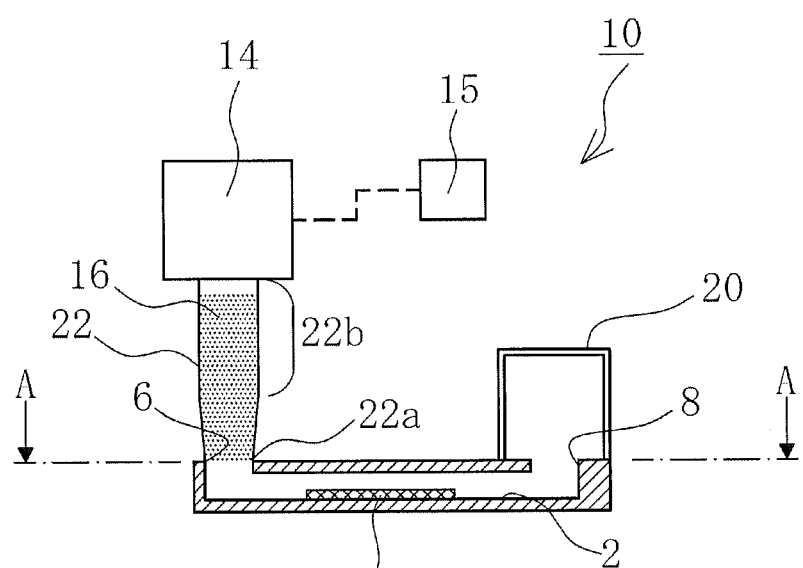
(b)
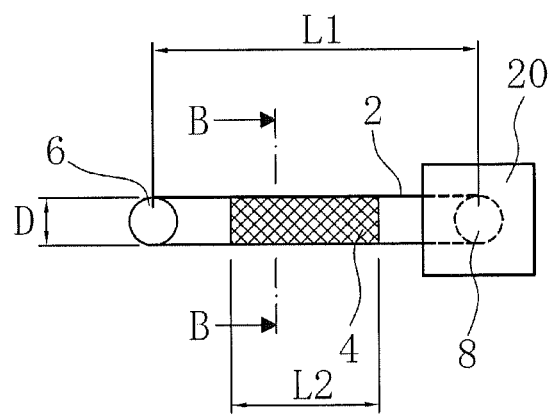
(c)
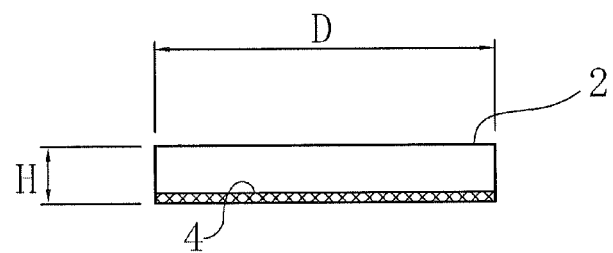

[Fig. 2]
(a)
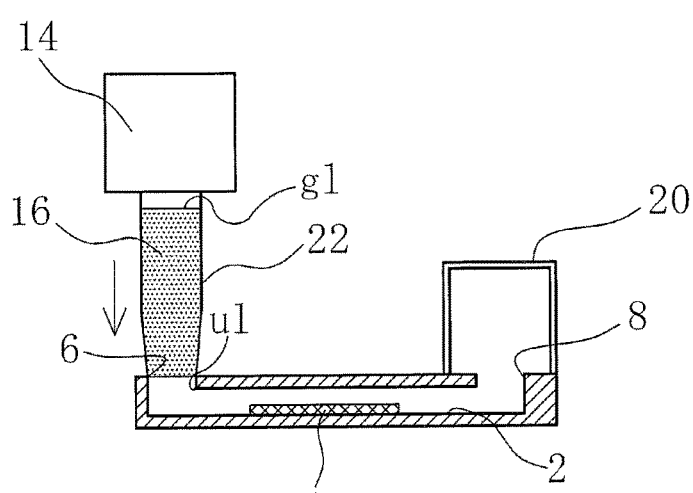
(b)
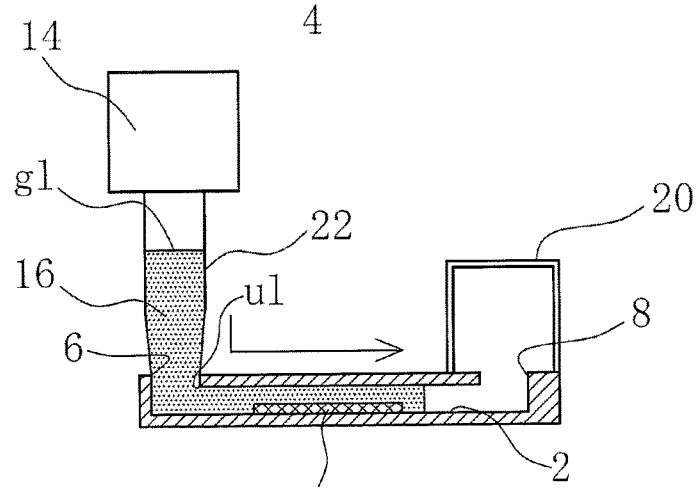
(c)
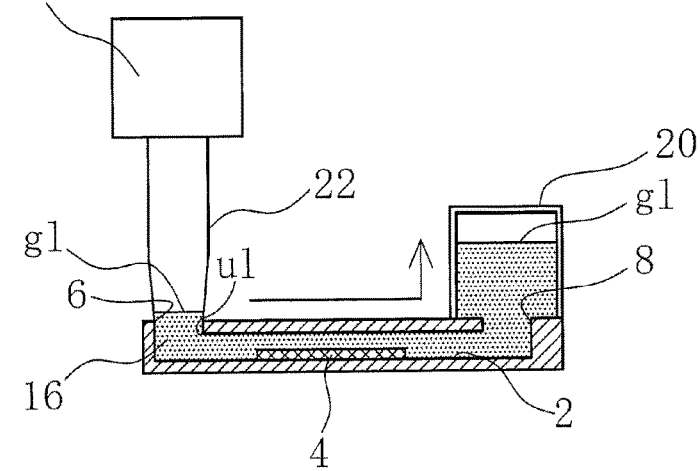

[Fig. 3]
(a)
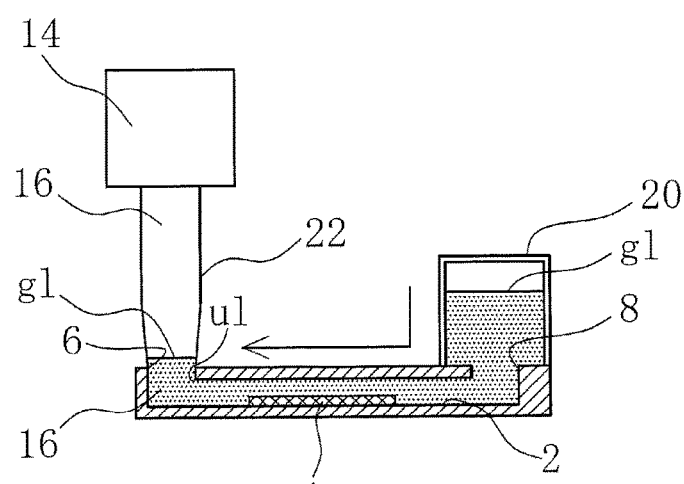
(b)
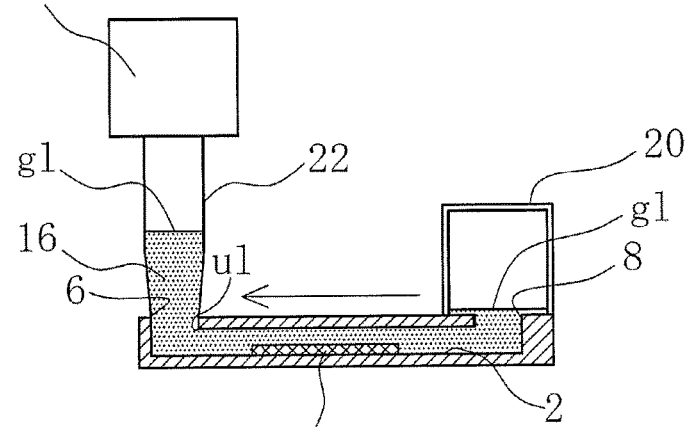
(c)
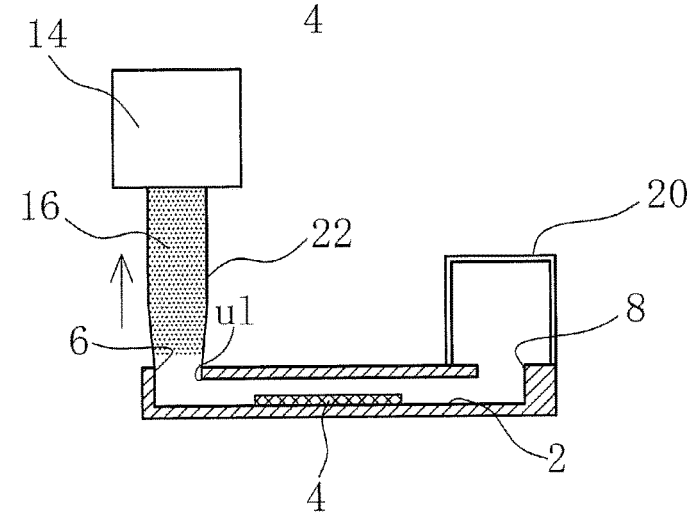

[Fig. 4]
(a)
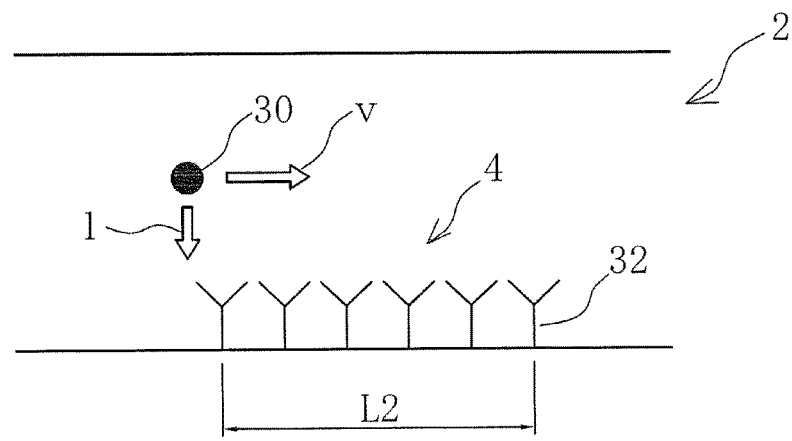
(b)
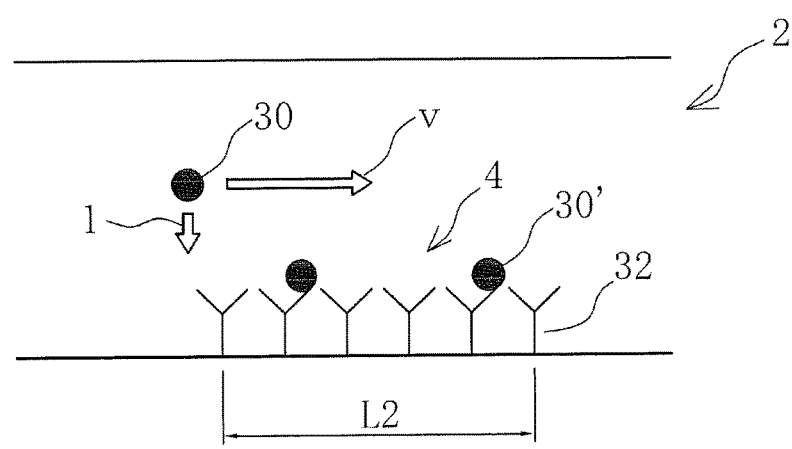
(c)
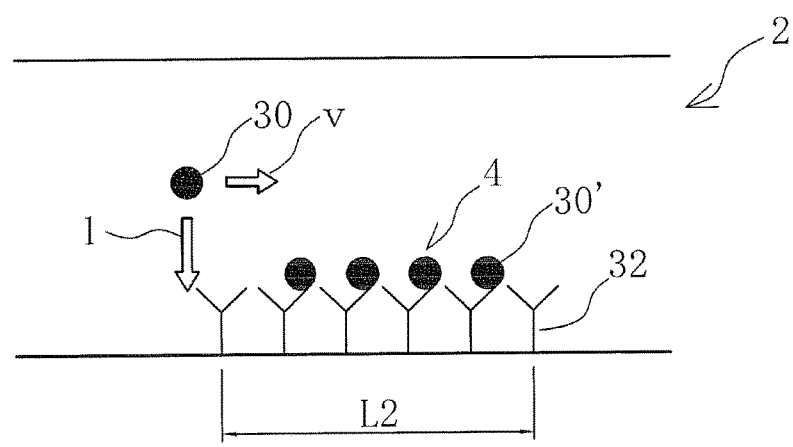

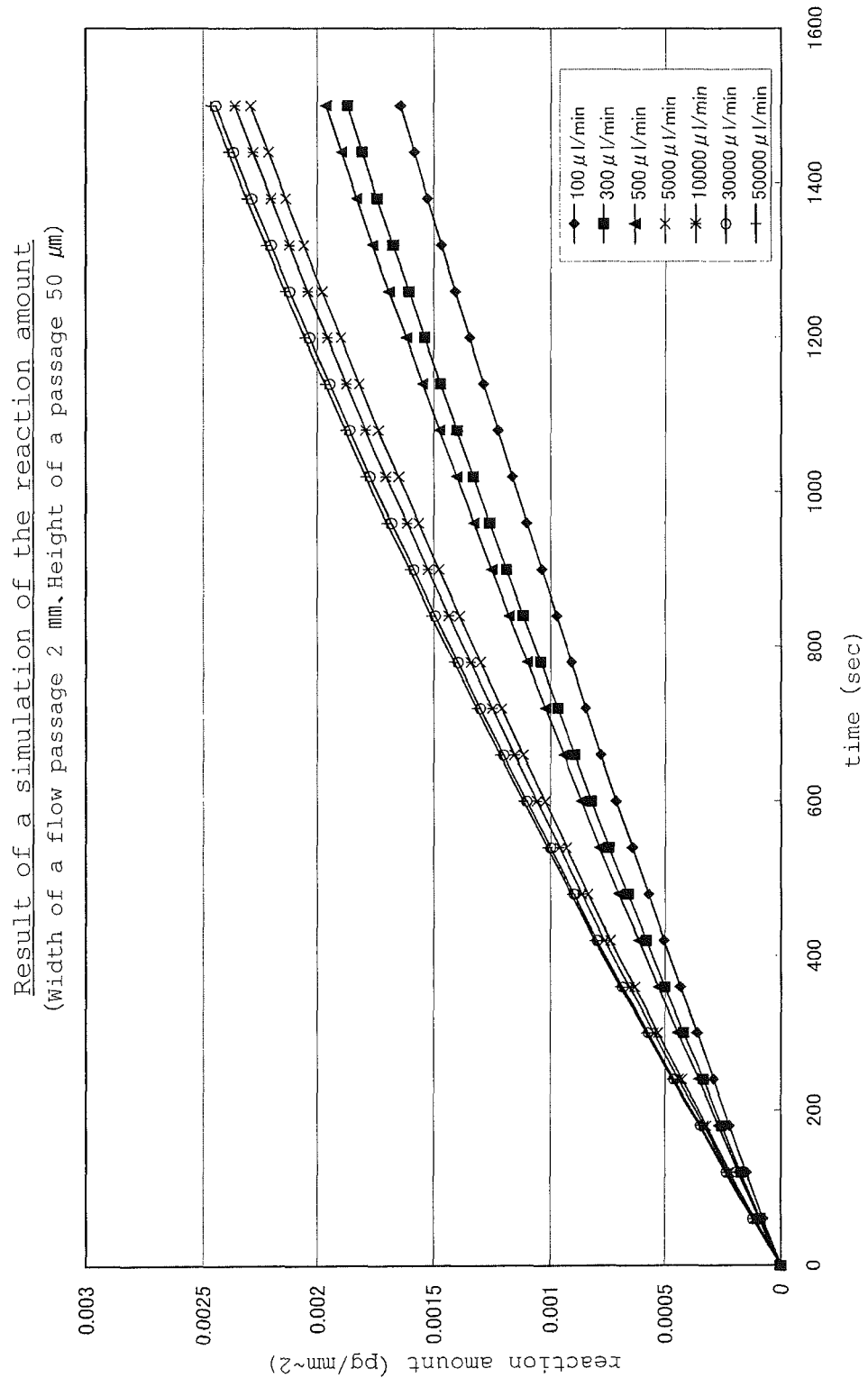

MICROCHIP SOLUTION SENDING SYSTEM

CROSS REFERENCE TO RELATED APPLICATIONS

The present application is a divisional application of U.S. patent application Ser. No. 13/153,838, filed on Jun. 6, 2011, the entire contents of which are incorporated herein by reference. The 13/153,838 application claimed the benefit of the date of the earlier filed Japanese Patent Application No. 2010-131970, filed Jun. 9, 2010, priority to which is also claimed herein, and the contents of which is also incorporated by reference herein.

BACKGROUND OF INVENTION

Technical Field

The present invention relates to a microchip solution sending system. More specifically, the present invention relates to a microchip solution sending system that is suitably utilized for an inspection and an analysis of a biological substance in which an antigen antibody reaction is used.

In the case in which a detection of an extremely fine substance is carried out, a wide variety of specimen material detection apparatus has been used for enabling an inspection of such an extremely fine substance by putting a physical phenomenon of a substance to practical use from the past.

As one of such specimen material detection apparatuses, there can be mentioned for instance a surface plasmon resonance apparatus (hereafter referred to as a SPR apparatus) in which a phenomenon for obtaining a high optical output by a resonance of an electron and a light in a minute region of a nanometer level or the like (a surface plasmon resonance (SPR: Surface Plasmon Resonance) phenomenon is put to practical use and an extremely fine analyte in a biological body is detected for instance.

As one of such specimen material detection apparatuses, there also can be mentioned for instance a surface plasmon field enhanced fluorescence spectroscopic measurement apparatus (hereafter referred to as a SPFS apparatus) in which the analyte detection can be carried out with a higher degree of accuracy as compared with the SPR apparatus based on a principle of a surface plasmon excitation enhanced fluorescence spectroscopy (SPFS: Surface Plasmon-field enhanced Fluorescence Spectroscopy) for putting a surface plasmon resonance (SPR) phenomenon to practical use.

For the above described specimen material detection apparatus, a specimen material solution that contains an analyte (antigen) that is a detection target is prepared in advance, the specimen material solution is sent to a fine flow passage, and an analyte (antigen) is captured with an antibody that is fixed to a reaction field that is disposed in the fine flow passage. The specimen material detection apparatus is provided with a microchip solution sending system for sending a specimen material solution into a fine flow passage most commonly.

As such a microchip solution sending system, there can be mentioned for instance a system that is called a circulation type in which a specimen material solution is circulated and passes through a reaction field in a repetitive manner (see FIG. 9) and a system that is called a reciprocation type in which a specimen material solution is reciprocated and passes through a reaction field in a repetitive manner (see FIG. 10) in addition to a system that is called a one pass type in which a specimen material solution passes through a reaction field only one time.

For a microchip solution sending system 100 of a circulation type shown in FIG. 9, an inlet side flow passage 110 and an outlet side flow passage 112 are connected to an inlet hole 106 and an outlet hole 108 of a fine flow passage 102, respectively, and the inlet side flow passage 110 and the outlet side flow passage 112 are connected to a circulation solution sending pump 114.

The circulation solution sending pump 114 performs a suction of a specimen material solution 116 from a specimen material solution container 118 that holds the specimen material solution 116, circulates the specimen material solution 116 to the inlet side flow passage 110, the fine flow passage 102, and the outlet side flow passage 112 in this order, and makes the specimen material solution 116 pass through a reaction field 104 in a repetitive manner. By this configuration, an analyte of a desired amount can be captured at the reaction field 104 even if an amount of the specimen material solution 116 is small (see Patent Literature 1 and Patent Literature 2 for instance).

For a microchip solution sending system 200 of a reciprocation type shown in FIG. 10, an inlet side flow passage 210 and an outlet side flow passage 212 are disposed at an inlet hole 206 and an outlet hole 208 of a fine flow passage 202, respectively, and a reciprocation solution sending pump 214 is connected to the inlet side flow passage 210. Moreover, the reciprocation solution sending pump 214 is connected to a specimen material solution container 218 that holds the specimen material solution 216.

By operating the reciprocation solution sending pump 214, the specimen material solution 216 that has been sucked from the specimen material solution container 218 is sent to the inlet side flow passage 210, the fine flow passage 202, and the outlet side flow passage 212 in this order.

Moreover, the reciprocation solution sending pump 214 enables a reciprocating movement of the specimen material solution 216 in the directions from one side to the other side and from the other side to one side. By this configuration, the specimen material solution 216 is then sent to the outlet side flow passage 212, the fine flow passage 202, and the inlet side flow passage 210 in this order, and passes through a reaction field 204 in a repetitive manner, whereby an analyte of a desired amount can be captured at the reaction field 204 even if an amount of the specimen material solution 216 is small (see Patent Literature 3 and Patent Literature 4 for instance).

For the conventional microchip solution sending systems 100 and 200 above described, a flow passage cross section of the fine flow passages 102 and 202 is in a generally rectangular shape, a width of the flow passage is approximately in the range of 0.5 mm to 3 mm, and a height of the flow passage is approximately in the range of 50 µm to 500 µm. A rate of flow of a specimen material solution that is sent to the fine flow passage is approximately in the range of 1 µl/min to 100 µl/min, and 500 µl/min or less even in the case in which an amount of a sent solution is large. As described above, the conventional microchip solution sending system is configured in such a manner that a solution is sent at a low rate region of flow of 500 µl/min or less even in the case in which a rate of flow of a specimen material solution that is sent to the fine flow passage is large. This is because a velocity of flow of a specimen material solution is small and the specimen material solution passes through a reaction field in a slow pace in the case in which a rate of flow of a specimen material solution is small, whereby the reaction efficiency in the case in which the specimen material solution passes through a reaction field becomes higher.

PRIOR ART DOCUMENTS

Patent Literature

[Patent Literature 1]
Japanese Patent Application Laid-Open Publication No. 2004-163259
[Patent Literature 2]
Japanese Patent Application Laid-Open Publication No. 2006-242912
[Patent Literature 3]
Japanese Patent Application Laid-Open Publication No. 2005-134372
[Patent Literature 4]
Japanese Patent Application Laid-Open Publication No. 2006-90985

However, since it is not said that the reaction efficiency is sufficiently high for the conventional microchip solution sending system above described, it is desired that the reaction efficiency of the conventional microchip solution sending system is further improved.

Moreover, for the conventional microchip solution sending system above described, the dispersion between individual pieces occurs for a reaction amount of an analyte that is detected in some cases. In other words, even in the case in which two microchip solution sending systems of the same specification are used under the same conditions, the reaction amounts of the analyte that is detected are different from each other in some cases. The dispersion of a reaction amount between individual pieces indicates a detection accuracy of the microchip solution sending system, and it is desired that the detection accuracy of the conventional microchip solution sending system is further improved.

SUMMARY OF INVENTION

As a result of that the present applicant has examined the conditions under such a situation with all heart and soul, in the case in which a solution sending is carried out in a high flow rate region that has not been used for a microchip solution sending system that is called a circulation type or a reciprocation type, the reaction efficiency can be further improved, and the dispersion of a reaction amount between individual pieces of the analytes that are detected can be suppressed from occurring. The present applicant has found the above effects and completed the present invention.

The present invention was made in order to solve the above problems of the conventional art. A microchip solution sending system in accordance with the present invention is characterized by comprising: a flow passage that is provided with a reaction field to which an antibody that reacts with a specific antigen is fixed; and a solution sending pump that is configured to send a specimen material solution that includes the specific antigen, wherein a specimen material solution passes through a reaction field of the flow passage in a repetitive manner in the case in which the solution sending pump sends the specimen material solution, and a flow rate of the specimen material solution that is sent by the solution sending pump is in the range of 1,000 µl/min to 50,000 µl/min.

BRIEF DESCRIPTION OF THE DRAWINGS

FIG. 1 is a schematic view for illustrating a microchip solution sending system in accordance with the present invention.

FIG. 2 is a schematic view for illustrating a flow of a specimen material solution for a microchip solution sending system in accordance with the present invention.

FIG. 3 is a schematic view for illustrating a flow of a specimen material solution for a microchip solution sending system in accordance with the present invention.

FIG. 4 is a schematic view for illustrating a relationship between a velocity of flow of a specimen material solution in a fine flow passage and the reaction efficiency of a reaction field.

FIG. 5 is a graph that indicates a result of a simulation of the reaction amount in the case in which a flow rate of a specimen material solution is changed for a microchip solution sending system in accordance with the present embodiment.

DETAILED DESCRIPTION OF THE PREFERRED EMBODIMENT

Figure 6:
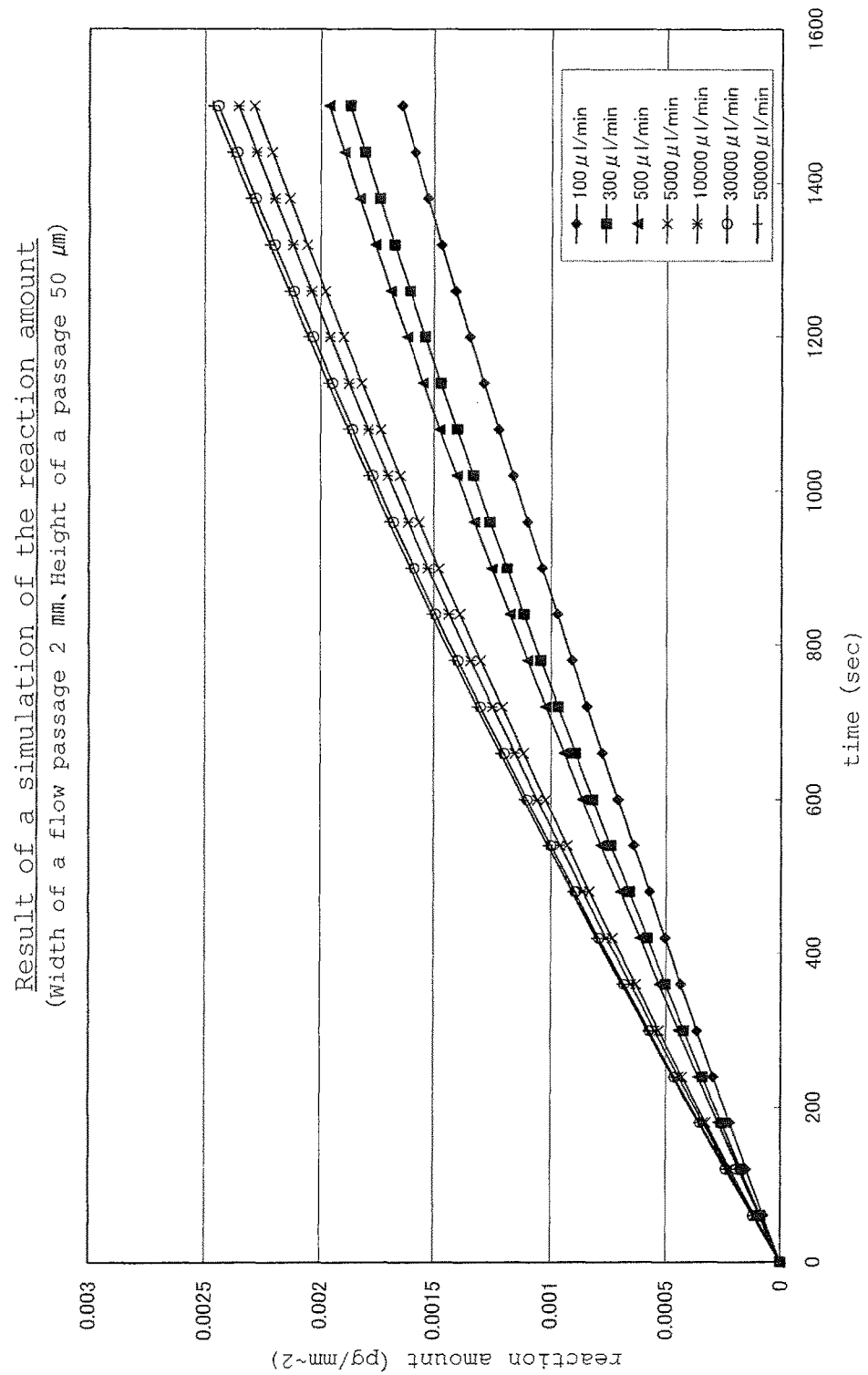
FIG. 6 is a graph that indicates a result of a simulation of the reaction amount in the case in which a flow rate of a specimen material solution is changed under the condition of the embodiment 1.

Hereinbelow, an embodiment of the present invention is described.

A microchip solution sending system in accordance with the present invention is characterized by comprising: a flow passage that is provided with a reaction field to which an antibody that reacts with a specific antigen is fixed; and a solution sending pump that is configured to send a specimen material solution that includes the specific antigen, wherein a specimen material solution passes through a reaction field of the flow passage in a repetitive manner in the case in which the solution sending pump sends the specimen material solution, and a flow rate of the specimen material solution that is sent by the solution sending pump is in the range of 1,000 µl/min to 50,000 µl/min.

By the above configuration, a flow rate of a specimen material solution that is sent by the solution sending pump can be in the range of a high flow rate region of 1,000 µl/min to 50,000 µl/min, whereby the reaction efficiency can be improved.

Moreover, the dispersion of a reaction amount between individual pieces of the analytes (antigens) that are captured with an antibody can be suppressed from occurring for the microchip solution sending systems of the same specification, whereby the detection accuracy can be improved.

The microchip solution sending system in accordance with the present invention is characterized by further comprising a mixing part that is connected to the flow passage in which the specimen material solution that has passed through the reaction field of the flow passage is stored temporarily and the specimen material solution that has been stored is stirred.

By comprising the above mixing part, the specimen material solution of a high flow rate region of 1,000 µl/min to 50,000 μl/min can be sent in a repetitive manner without reducing the reaction efficiency for the microchip solution sending system of so-called a circulation type and the microchip solution sending system of a reciprocation type in which the specimen material solution passes through the reaction field of the flow passage in a repetitive manner.

The microchip solution sending system in accordance with the present invention is characterized in that a cross section of the flow passage is in a rectangular shape, and a width of the flow passage is in the range of 0.5 mm to 3 mm and a height of the flow passage is in the range of 50 μm to 500 μm preferably.

It is not necessarily that the rectangular shape of a cross section of the flow passage is a perfect rectangular shape. The rectangular shape can be a shape that is considered as a substantive rectangular shape as a whole of a flow passage cross section. Consequently, the above rectangular shape can also include a tapered shape or an R shape of a corner part and a slight concave-convex shape of a whole or a part of a side for instance.

By the above configuration, in the case in which a flow rate of the specimen material solution that is sent by the solution sending pump is in the range of a high flow rate region of 1,000 μl/min to 50,000 μl/min, the reaction efficiency can be improved and the detection accuracy can be improved, whereby the features of the microchip solution sending system in accordance with the present invention can be displayed more preferably.

Moreover, in the case in which a flow rate of the specimen material solution that is sent by the solution sending pump is in the range of 5,000 μl/min to 50,000 μl/min, the effects of the present invention can be displayed more preferably.

A specimen material detection apparatus in accordance with the present invention is characterized by comprising any one of the microchip solution sending systems above described.

By the above configuration, the reaction efficiency can be improved as compared with a specimen material detection apparatus that is provided with a conventional microchip solution sending system, and the specimen material detection apparatus can be provided with a high accuracy with a small dispersion between individual pieces.

The specimen material detection apparatus in accordance with the present invention is characterized in that the specimen material detection apparatus is a surface plasmon resonance apparatus (a SPR apparatus) or a surface plasmon field enhanced fluorescence spectroscopic measurement apparatus (a SPFS apparatus).

In the case in which the specimen material detection apparatus is a surface plasmon resonance apparatus (a SPR apparatus) or a surface plasmon field enhanced fluorescence spectroscopic measurement apparatus (a SPFS apparatus) as described above, the specimen material detection apparatus is suitable as detection apparatus of an extremely minute analyte in particular. Moreover, the reaction efficiency can be improved as compared with a SPR apparatus or a SPFS apparatus that is provided with a conventional microchip solution sending system, and the SPR apparatus or the SPFS apparatus can be provided with a high accuracy with a small dispersion between individual pieces.

In accordance with the present invention, for a microchip solution sending system that is called a circulation type or a reciprocation type in which a specimen material solution passes through a reaction field of a flow passage in a repetitive manner, a flow rate of the specimen material solution that is sent by the solution sending pump is in the range of a high flow rate region of 1,000 μl/min to 50,000 μl/min, whereby the reaction efficiency can be improved, and thereby providing a microchip solution sending system that is provided with a high accuracy with a small dispersion of a reaction amount between individual pieces of the analytes that are detected and a high-accuracy specimen material detection apparatus that is provided with the microchip solution sending system.

An embodiment (example) of the present invention will be described below in detail with reference to the drawings. While the preferred embodiments in accordance with the present invention will be described in the following, the present invention is not restricted to the embodiments.

<Microchip solution sending system 10>

FIG. 1 is a schematic view for illustrating a microchip solution sending system 10 in accordance with the present invention. FIG. 1(a) is a cross-sectional view showing the microchip solution sending system 10. FIG. 1(b) is an A-A view of the microchip solution sending system 10 in accordance with the present invention taken along the line A-A viewed from the direction of the arrows A of FIG. 1(a). FIG. 1(c) is a B-B view of the microchip solution sending system 10 in accordance with the present invention taken along the line B-B viewed from the direction of the arrows B of FIG. 1(b).

As shown in FIG. 1(a), the microchip solution sending system 10 in accordance with the present invention is provided with a fine flow passage 2 and a solution sending pump 14 that is configured to send a specimen material solution 16. Moreover, a reaction field 4 to which an antibody of a predetermined amount that reacts with a specific antigen is fixed is disposed on the bottom surface in the fine flow passage 2. In the case in which the solution sending pump 14 sends the specimen material solution 16 that includes a specific antigen (analyte), the specimen material solution 16 passes through the reaction field 4 of the fine flow passage 2 in a repetitive manner.

For the microchip solution sending system 10 in accordance with the present invention, although a shape of a cross section of the fine flow passage 2 is not restricted in particular, the cross section of the fine flow passage 2 is in a generally rectangular shape in the present embodiment. In the case in which the cross section of the fine flow passage 2 is in a generally rectangular shape, it is preferable that a width D of the flow passage of the fine flow passage 2 is in the range of 0.5 mm to 3 mm and a height H of the flow passage of the fine flow passage 2 is in the range of 50 μm to 500 μm. In the present embodiment, D=2 mm and H=50 μm.

Moreover, a length L1 of the flow passage of the fine flow passage 2 is in the range of 2 mm to 30 mm preferably, and in the range of 2 mm to 20 mm more preferably. In the present embodiment, L1=14 mm.

A forming range of the reaction field 4 is appropriately configured in consideration of a shape of the fine flow passage 2 and an amount of an analyte that is supplied in such a manner that an analyte of a desired amount can be captured in an efficient manner. In the present embodiment, the reaction field 4 is formed along the whole width of the bottom surface, and a length L2 in the direction of the flow passage is 2 mm.

As shown in FIGS. 1(a) and 1(b), an inlet hole 6 that is an inlet for flowing the specimen material solution 16 into the fine flow passage 2 is formed on one end side in the direction of the flow passage of the fine flow passage 2, and an outlet hole 8 that is an outlet of the specimen material solution 16 that has been flown from the inlet hole 6 is formed on the other end side in the direction of the flow passage of the fine flow passage 2. For the microchip solution sending system 10 in accordance with the present invention, it is preferable that the diameter of the inlet hole 6 and the outlet hole 8 is in the range of φ0.5 mm to φ3 mm, which is almost equivalent to the width D of the flow passage of the fine flow passage 2. In the present embodiment, the diameter is φ2 mm.

As shown in FIG. 1(*a*), a pipette 22 that holds the specimen material solution 16 is connected to the upper face side of the inlet hole 6. An end 22*a* of the pipette 22 is in a cross sectional shape that is almost equivalent to that of the inlet hole 6, and the pipette 22 is configured in a detachable manner from the inlet hole 6 of the fine flow passage 2. A diameter of a base end part 22*b* of the pipette 22 is larger than that of the end 22*a*. In the present embodiment, the specimen material solution 16 of 100 μl is held in the pipette 22.

The solution sending pump 14 is attached to the upper part of the pipette 22. The solution sending pump 14 communicates with a control part 15. In accordance with the command from the control part 15, the solution sending pump 14 discharges the specimen material solution 16 that has been held in the pipette 22 to the fine flow passage 2, and performs a suction of the specimen material solution 16 that has been stored in the fine flow passage 2 or in a mixing part 20 described later into the pipette 22. Moreover, the solution sending pump 14 can send the specimen material solution 16 in the range of a high flow rate region of 1,000 μl/min to 50,000 μl/min.

As shown in FIG. 1(*a*), the mixing part 20 is connected to the upper face side of the outlet hole 8. Across sectional shape of the mixing part 20 is a rectangular shape or a circular shape that is larger than a cross sectional shape of the outlet hole 8, and one side of the cross sectional shape of the mixing part 20 is in the range of 5 mm to 12 mm for instance. In the present embodiment, the mixing part 20 is in a generally square shape of which one side is 8 mm.

A flowing operation of the microchip solution sending system 10 in accordance with the present embodiment will be described with reference to FIGS. 2 and 3. FIGS. 2(*a*) to 2(*c*) and 3(*a*) to 3(*c*) are schematic views for illustrating a flow of the specimen material solution 16 for the microchip solution sending system 10 in accordance with the present invention. The arrows of FIGS. 2 and 3 indicate a solution sending direction of the specimen material solution 16. A sign gl indicates an interfacial boundary surface between the specimen material solution 16 and an air, that is, an air-liquid interface, and a sign ul indicates a height of the upper face of the flow passage of the fine flow passage 2.

FIG. 2(*a*) shows the state in which the pipette 22 that holds the specimen material solution 16 is mounted to the inlet hole 6 of the fine flow passage 2 and the solution sending pump 14 is attached to the pipette 22.

In the case in which the solution sending pump 14 is driven and the specimen material solution 16 that has been held in the pipette 22 is discharged in the state shown in FIG. 2(*a*), the specimen material solution 16 is flown into the fine flow passage 2 via the inlet hole 6 and a part of the specimen material solution 16 passes over the reaction field 4 as shown in FIG. 2(*b*).

In the case in which the solution sending pump 14 further discharges the specimen material solution 16 that has been held in the pipette 22 from this state, the most of the specimen material solution 16 in the pipette 22 is flown into the fine flow passage 2 via the inlet hole 6 and an air-liquid interface gl in the pipette 22 is lowered close to the height ul of the upper face of the flow passage of the fine flow passage 2 as shown in FIG. 2(*c*). In addition, the specimen material solution 16 that has passed over the reaction field 4 is flown into the mixing part 20 via the outlet hole 8, and an air-liquid interface gl in the mixing part 20 moves upward.

The solution sending pump 14 is then driven in order to suck the specimen material solution 16 in this state. By this operation, a solution sending direction of the specimen material solution 16 is then reversed as shown in FIG. 3(*a*). The specimen material solution 16 in the mixing part 20 is then flown into the fine flow passage 2 via the outlet hole 8, passes over the reaction field 4 again, and is flown into the pipette 22 via the inlet hole 6. An air-liquid interface gl in the pipette 22 moves upward, and an air-liquid interface gl in the mixing part 20 is lowered close to the height ul of the upper face of the flow passage of the fine flow passage 2 as shown in FIG. 3(*b*).

The solution sending pump 14 is then driven in order to discharge the specimen material solution 16 in the state shown in FIG. 3(*b*). By this operation, a solution sending direction of the specimen material solution 16 is then reversed again. The specimen material solution 16 in the pipette 22 is then flown into the fine flow passage 2 via the inlet hole 6, passes over the reaction field 4 again, and is flown into the mixing part 20 via the outlet hole 8 in the state shown in FIG. 2(*c*).

In the case in which the specimen material solution 16 is recovered, after the solution sending pump 14 performs a suction of the specimen material solution 16 to the state shown in FIG. 3(*c*), the pipette 22 that holds the specimen material solution 16 can be detached.

For the microchip solution sending system 10 in accordance with the present embodiment as described above, the states of FIG. 2(*c*), FIG. 3(*a*), FIG. 3(*b*), and FIG. 2(*c*) are transferred in a repetitive manner by operating the discharge and the suction using the solution sending pump 14 in a repetitive manner, whereby the specimen material solution 16 passes over the reaction field 4 in the fine flow passage 2 in a repetitive manner.

In this case, it is preferable that the switching of a driving state of the solution sending pump 14 is carried out in such a manner that an air-liquid interface gl in the pipette 22 and in the mixing part 20 is not lower than the height ul of the upper face of the flow passage of the fine flow passage 2. By this configuration, an air is not mixed into the fine flow passage 2, whereby a failure that may occur due to a mixture of an air into the fine flow passage 2 can be prevented, for instance, a deterioration of a solution sending ability due to an increase in a solution sending resistance and a reduction of the reaction efficiency due to a mixed air that covers the reaction field 4 can be prevented.

It is preferable that the microchip solution sending system 10 in accordance with the present invention is configured as described in the following in order to automatically switch a driving state of the solution sending pump 14.

That is, it is preferable that a sensor that is configured to measure an air-liquid interface gl is disposed in at least one of the pipette 22 and the mixing part 20 in order to automatically switch a driving state of the solution sending pump 14. In the case in which an air-liquid interface gl is equal to or less than the predetermined level, a signal is sent from the sensor to the control part 15, and the control part 15 issues the command to the solution sending pump 14 to switch a driving state.

Moreover, it also can be set that a driving state is automatically switched in the case in which the solution sending pump 14 sends the specimen material solution 16 of a predetermined amount that has been specified in advance, whereby a driving state of the solution sending pump 14 can be automatically switched. For instance, a difference that is obtained by subtracting a stored amount of the specimen material solution 16 in the pipette 22 in the state shown in FIG. 3(a) from a stored amount of the specimen material solution 16 in the pipette 22 in the state shown in FIG. 3(b) is set to the control part 15 in advance as an amount of a solution to be sent by the solution sending pump 14. In the case in which an amount of the specimen material solution 16 that is discharged (or sucked) by the solution sending pump 14 reaches the above amount, a driving state of the solution sending pump 14 can be automatically switched.

In the next place, an effect of an installation of the mixing part 20 will be described in the following.

Figure 10:
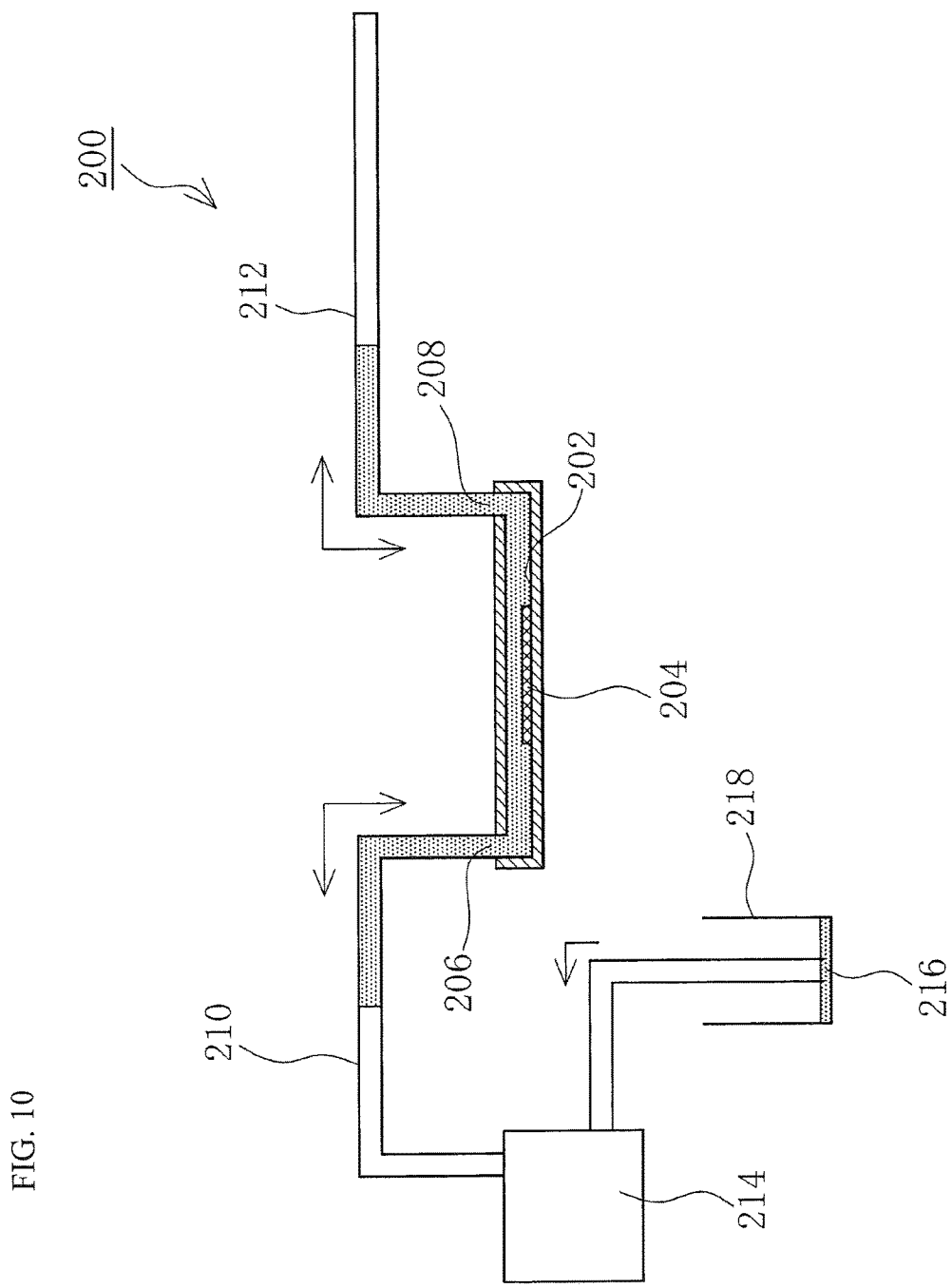
FIG. 10 is a schematic view showing a conventional microchip solution sending system of a reciprocation type.

The specimen material solution is flown in the fine flow passage 2 in a laminar flow state, that is, a state in which the streamlines of fluids are generally parallel to each other on a constant basis for the microchip solution sending system. Consequently, in the case in which the specimen material solution 216 is reciprocated simply like the conventional microchip solution sending system 200 shown in FIG. 10 for instance, the specimen material solution 216 of the same layer comes into contact with the reaction field 204 on a constant basis. As a result, only a part of the specimen material solution 216 contributes to a reaction on the reaction field 204.

On the other hand, the microchip solution sending system 10 in accordance with the present embodiment is provided with the mixing part 20 with a cross sectional shape larger than a cross section of the fine flow passage 2. Consequently, in the case in which the specimen material solution 16 is flown into the mixing part 20, the specimen material solution 16 that is stored in the mixing part 20 is stirred due to a turbulence of a flow of the specimen material solution 16 that has been flown in a laminar flow state. Accordingly, even in the case in which the specimen material solution 16 passes on the reaction field 4 in a repetitive manner, only the same layer does not come into contact with the reaction field 4, and most of the specimen material solution 16 contributes to a reaction on the reaction field 4. Moreover, the specimen material solution 16 that is stored in the pipette 22 is also stirred similarly.

Consequently, since the mixing part 20 above described is disposed for the microchip solution sending system 10 in accordance with the present invention in which the specimen material solution 16 passes on the reaction field 4 in the fine flow passage 2 in a repetitive manner, the reaction efficiency can be prevented from being reduced and the specimen material solution 16 of a high flow rate region in the range of 1,000 μl/min to 50,000 μl/min can be sent in a repetitive manner.

<Effect of Sending the Specimen Material Solution 16 in a High Flow Rate Region>

In the next place, the following describes an effect of sending the specimen material solution 16 in a high flow rate region in the range of 1,000 μl/min to 50,000 μl/min for the microchip solution sending system 10 described above.

A rate of flow that is described here means an amount of a fluid that is flown in a unit time and is indicated by μl/min. Moreover, a velocity of flow is obtained by dividing a rate of flow by a cross sectional area of a flow passage and means a distance in which a fluid moves in a unit time. The velocity of flow is indicated by mm/min or mm/sec.

FIG. 4 is a schematic view for illustrating a relationship between a velocity v of flow of the specimen material solution 16 in the fine flow passage 2 and the reaction efficiency of the reaction field 4. A sign v in FIG. 4 indicates a velocity of flow of the specimen material solution 16 that is flown in the fine flow passage 2, and a sign 1 indicates a diffusion distance of an analyte (antigen) 30. A size of an arrow of the velocity v of flow and the diffusion distance 1 indicates a degree of a velocity of flow and a degree of a diffusion distance, respectively.

Here, a time t that is required for the analyte 30 shown in FIG. 4(a) to pass on the reaction field 4 is represented by the expression (1).

[Expression 1]

$$t = L2/v \quad (1)$$

Here, L2 indicates a length of the reaction field 4, and v indicates a rate of flow of the specimen material solution 16.

Moreover, the diffusion distance 1 in which the analyte 30 shown in FIG. 4(a) moves in the bottom surface direction when passing on the reaction field 4 is represented by the expression (2).

[Expression 2]

$$1 = \sqrt{(t \times D)} \quad (2)$$

Here, the time t is required for the analyte 30 to pass on the reaction field 4 and is a time that is calculated by the expression (1), and D is a diffusion constant.

As clarified by the expressions (1) and (2), as the velocity v of flow of the specimen material solution 16 is higher, the time t that is required for the analyte 30 to pass on the reaction field 4 is shorter, whereby the diffusion distance 1 is smaller. On the other hand, as the velocity v of flow of the specimen material solution 16 is lower, the time t that is required for the analyte 30 to pass on the reaction field 4 is longer, whereby the diffusion distance 1 is larger.

As the diffusion distance 1 of the analyte 30 is smaller, the number of the analytes 30 that are captured with an antibody 32 is less as shown in FIG. 4(b). On the other hand, as the diffusion distance 1 of the analyte 30 is larger, the number of the analytes 30 that are captured with an antibody 32 is larger as shown in FIG. 4(c).

As described above, as the velocity v of flow of the specimen material solution 16 is lower, the diffusion distance 1 of the analyte 30 is larger and the number of the analytes 30 that are captured with an antibody 32 is larger. Consequently, for the conventional microchip solution sending system, it is a technical common knowledge that the specimen material solution is sent in the range of a low rate region of flow of 1 μl/min to 500 μl/min for instance in such a manner that a rate of flow of the specimen material solution is lower even for a circulation type and a reciprocation type as well as a one pass type.

However, for the microchip solution sending system 10 in accordance with the present embodiment as described above in which the specimen material solution 16 passes on the reaction field 4 in a repetitive manner, sending the specimen material solution 16 in the range of a low rate region of flow dose not always result in an improvement of the reaction efficiency. It has been found that the reaction efficiency can be improved in the case in which the specimen material solution 16 is sent in the range of a high rate region of flow.

This means that an effect of increasing a flow rate in a unit time and increasing the number of passing on the reaction field contributes to an improvement of the reaction efficiency rather than increasing the diffusion distance 1 under the condition in which a measuring time, that is, a reaction time is constant. However, the effect can be obtained only for the microchip solution sending system in which the specimen material solution 16 passes on the reaction field 4 in a repetitive manner like the present invention. For the conventional microchip solution sending system of a one pass type, in the case in which the velocity of flow of the specimen material solution is higher, the time t that is required for the analyte 30 to pass on the reaction field 4 is shorter, whereby the reaction efficiency is reduced.

FIG. 5 and Table 1 indicate a result of a simulation of the reaction amount in a unit area in the case in which a flow rate of the specimen material solution 16 is in a low flow rate region of 100 μl/min, 300 μl/min, and 500 μl/min (a comparative example) and is in a high flow rate region of 1,000 μl/min, 5,000 μl/min, 10,000 μl/min, 30,000 μl/min, and 50,000 μl/min (the present embodiment) for the microchip solution sending system 10 in accordance with the present embodiment described above. A vertical axis of FIG. 5 represents a reaction amount in a unit area of the reaction field 4, and a horizontal axis represents a measuring time. The conditions of an effective antibody density of the reaction field 4 and an amount of an antibody in the specimen material solution 16 in the case of the present embodiment are set to be equivalent to those in the case of the comparative example.

(Conditions)

Measuring time: 1500 sec

Width of a flow passage: 2 mm

Height of a flow passage: 50 μm

Shape of a reaction field: 2 mm×2 mm

Amount of a specimen material solution: 100 μl

TABLE 1

| Flow rate (μl/min) | Amount of a specimen material solution (μl) | Effective antibody density (mol/cm$^2$) | Amount of an antigen (pg) | Number of passing (times/min) | Reaction amount in a unit area (pg/mm$^2$) | Note |
|---|---|---|---|---|---|---|
| 100 | 100 | 6.70 × 10$^{-12}$ | 0.0175 | 1 | 0.00136 | Comparative example |
| 300 | | | | 3 | 0.00156 | |
| 500 | | | | 5 | 0.00164 | |
| 1,000 | | | | 10 | 0.00187 | Embodiment |
| 5,000 | | | | 50 | 0.00192 | |
| 10,000 | | | | 100 | 0.00198 | |
| 30,000 | | | | 300 | 0.00205 | |
| 50,000 | | | | 500 | 0.00208 | |

Table 2 indicates a result of an actual measurement of the fluorescence intensity in the case in which a flow rate of the specimen material solution 16 is in a low flow rate region of 100 μl/min, 300 μl/min, and 500 μl/min (a comparative example) and is in a high flow rate region of 1,000 μl/min, 5,000 μl/min, 10,000 μl/min, 30,000 μl/min, and 50,000 μl/min (the present embodiment) for the SPFS apparatus that is provided with the microchip solution sending system 10 in accordance with the present embodiment described above.

For the SPFS apparatus, as the number of the analytes 30 that have been captured is larger, that is, as a reaction amount in a unit area is larger, the higher fluorescence intensity is measured.

TABLE 2

| Flow rate (μl/min) | Amount of a specimen material solution (μl) | Effective antibody density (mol/cm$^2$) | Amount of an antigen (pg) | Number of passing (times/min) | Fluorescence intensity | Note |
|---|---|---|---|---|---|---|
| 100 | 100 | 6.70 × 10$^{-12}$ | 0.0175 | 1 | 24,800 | Comparative example |
| 300 | | | | 3 | 28,500 | |
| 500 | | | | 5 | 30,000 | |
| 1,000 | | | | 10 | 34,100 | Embodiment |
| 5,000 | | | | 50 | 35,100 | |
| 10,000 | | | | 100 | 36,200 | |
| 30,000 | | | | 300 | 37,600 | |
| 50,000 | | | | 500 | 38,100 | |

As clarified by FIG. 5 and Table 1, at the point of time when a measuring time (1500 sec) elapses, as a rate of flow is higher, a reaction amount in a unit area is larger. A tendency of the simulation result can also be confirmed by a result of an actual measurement of the fluorescence intensity shown in Table 2.

This means that the reaction efficiency can be improved in the case in which a velocity of flow is made to be higher and the number of passing of the specimen material solution 16 on the reaction field 4 is made to be increased rather than the case in which a velocity of flow is made to be lower for the microchip solution sending system 10 in accordance with the present invention in which the specimen material solution 16 passes on the reaction field 4 in a repetitive manner.

As clarified by FIG. 5 and Table 1, a variation of a reaction amount that is associated with a variation of a rate of flow is smaller in the case of a high flow rate region (the present embodiment) as compared with the case of a low flow rate region (a comparative example). A tendency of the simulation result can also be confirmed by a result of an actual measurement of the fluorescence intensity shown in Table 2.

For the microchip solution sending system 10 in accordance with the present invention, a rate of flow of the specimen material solution 16 that is sent depends on an ability of the solution sending pump 14. The solution sending pump 14 is configured in such a manner that the specimen material solution 16 is discharged or sucked at a predetermined pressure, and is not configured in such a manner that a predetermined rate of flow is discharged or sucked directly. Consequently, even in the case in which the specimen material solution 16 is sent under the same conditions for two microchip solution sending systems 10 of the same specification, the rates of flow of the specimen material solutions 16 that are sent by the solution sending pump 14 as a practical matter are slightly different from each other due to an influence of a dimensional tolerance of a shape of the fine flow passage 2.

As described above, a variation of a reaction amount that is associated with a variation of a rate of flow is smaller in the case of a high flow rate region. This means that the dispersion of a reaction amount between individual pieces due to an influence of the dispersion of a width of a flow passage, a height of a flow passage, and a rate of flow of the microchip solution sending system 10 can be reduced, that is, a detection accuracy of the microchip solution sending system 10 can be improved preferably in the case in which the specimen material solution 16 is sent in a high flow rate region.

For the present invention, a variation of a reaction amount that is associated with a variation of a rate of flow is smaller in the case in which the specimen material solution 16 is sent in a high flow rate region as described above. It is inferable that this is because a reaction of the analyte 30 with an antibody 32 becomes in the state close to a rate determining reaction in the state of a high flow rate region as compared with the state of a low flow rate region.

In other words, in order to improve the reaction efficiency of the analyte 30 with an antibody 32, it is thought that a reaction condition is increased (that is, an amount of an antibody 32 that is fixed to the reaction field 4 is increased) in addition to that a diffusion condition is increased (that is, the velocity v of flow of the specimen material solution 16 is lowered and the diffusion distance 1 is enlarged) and a supply condition is increased (that is, a rate of flow of the specimen material solution 16 is increased and an amount of the analyte 30 that is supplied to the reaction field 4 is increased). In the state in which a diffusion condition and a supply condition are increased for a certain amount of an antibody and the diffusion condition and the supply condition are satisfied sufficiently, the reaction efficiency is not further improved even if the diffusion condition and the supply condition are further increased. In other words, the reaction efficiency becomes in the state of a rate determining reaction that is controlled by the reaction condition mainly.

In the state of such a rate determining reaction, the reaction efficiency is not further improved even if of a rate of flow of the specimen material solution 16 is increased. For the present invention, a variation of a reaction amount that is associated with a variation of a rate of flow is smaller in the case in which the specimen material solution 16 is sent in a high flow rate region as described above. It is thought that this is because a reaction becomes in the state close to a rate determining reaction in the case in which a rate of flow of the specimen material solution 16 is in the range of a high flow rate region of 1,000 µl/min to 50,000 µl/min as compared with the conventional case in which the specimen material solution 16 is sent in a low flow rate region.

Moreover, in the case in which the specimen material solution 16 is sent at a flow rate that exceeds 50,000 µl/min, an extremely large solution sending ability is required for the solution sending pump 14, and an extremely high pressure is applied to the fine flow passage 2. Consequently, an extremely high manufacturing quality is required for the fine flow passage 2 that includes the reaction field 4, whereby it is difficult to configure the microchip solution sending system suitable for practical use. Therefore, it is preferable that a rate of flow of the specimen material solution 16 is equal to or less than 50,000 µl/min.

As described above in detail, for the microchip solution sending system 10 in accordance with the present invention, in the case in which a rate of flow of the specimen material solution 16 that is sent by the solution sending pump 14 is in the range of a high flow rate region of 1,000 µl/min to 50,000 µl/min, the reaction efficiency can be improved. Moreover, the dispersion of a reaction amount between individual pieces of the analytes that are detected can be suppressed from occurring for the microchip solution sending systems 10 of the same specification, whereby the detection accuracy can be improved.

The microchip solution sending system 10 in accordance with the present embodiment described above is a microchip solution sending system of so-called a reciprocation type. However, the microchip solution sending system 10 in accordance with the present invention is not restricted to the above configuration, and the microchip solution sending system 10 in accordance with the present invention can also be configured as a microchip solution sending system of so-called a circulation type as shown in FIG. 8.

Figure 8:
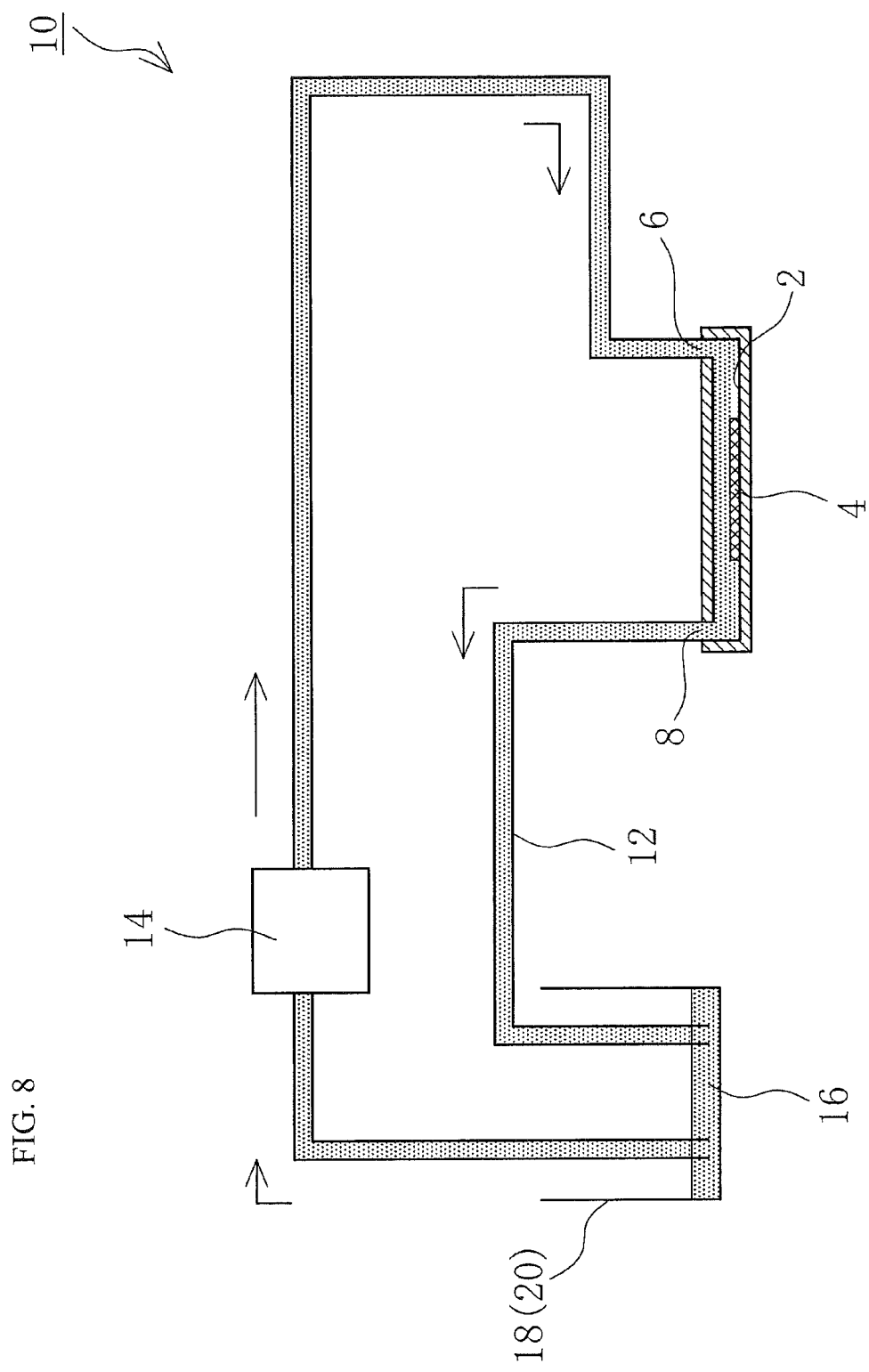
FIG. 8 is a schematic view showing a microchip solution sending system in accordance with another embodiment of the present invention.
Figure 9:
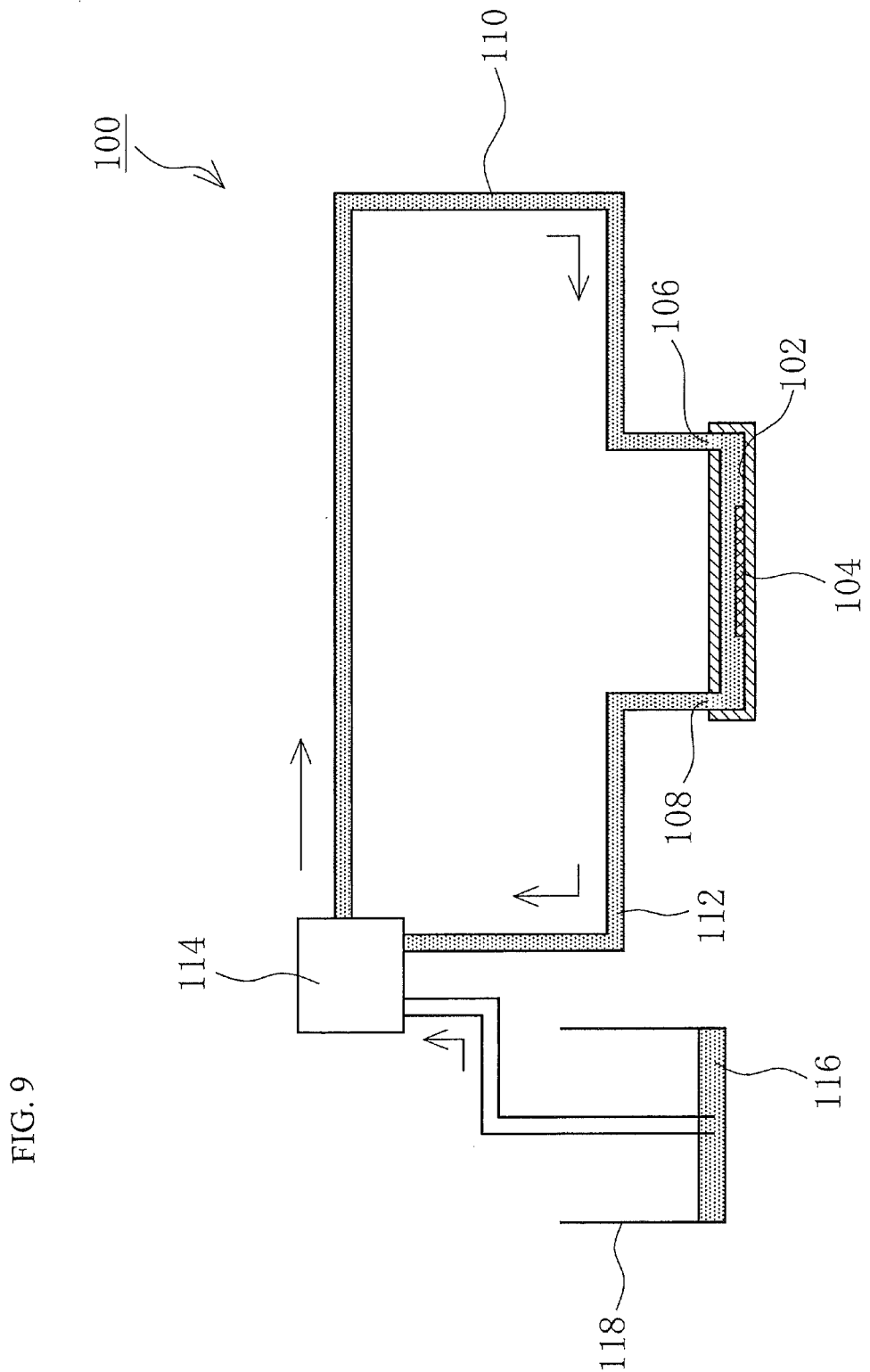
FIG. 9 is a schematic view showing a conventional microchip solution sending system of a circulation type.

The microchip solution sending system 10 in accordance with the present invention shown in FIG. 8 is different from the conventional microchip solution sending system 100 of a circulation type shown in FIG. 9 described above at the point of that the specimen material solution container 18 also functions as the mixing part 20.

In other words, for the microchip solution sending system 10 of a circulation type shown in FIG. 8, the outlet side flow passage 12 is not connected directly to the solution sending pump 14 and is connected to the solution sending pump 14 via the specimen material solution container 18 unlike the conventional microchip solution sending system 100 of a circulation type. By the above configuration, the specimen material solution 16 that is flown via the outlet side flow passage 12 and that is stored in the specimen material solution container 18 on a temporary basis is stirred. Consequently, the specimen material solution container 18 also performs a function equivalent to that of the mixing part 20 in accordance with the embodiment described above, whereby the specimen material solution 16 in the range of a high flow rate region of 1,000 µl/min to 50,000 µl/min can be sent in a repetitive manner without reducing the reaction efficiency.

For a wide variety of numerical value ranges in accordance with the present specification, the numerical value itself is also included in the numerical value range. For instance, 1,000 µl/min to 50,000 µl/min means that it is equal to or larger than 1,000 µl/min and equal to or less than 50,000 µl/min.

[Embodiments]

The result of the simulation that has been carried out to confirm the effect of the microchip solution sending system 10 in accordance with the present invention will be described in the following.

[Embodiment 1]

In the present embodiment, for the microchip solution sending system 10 described above, the reaction amount in a unit area was simulated in the case in which a width of the flow passage of the fine flow passage 2 is 1 mm, a height of the flow passage of the fine flow passage 2 is 50 µm, and a flow rate of the specimen material solution 16 is in a low flow rate region of 100 µl/min, 300 µl/min, and 500 µl/min (a comparative example) and is in a high flow rate region of 1,000 µl/min, 5,000 µl/min, 10,000 µl/min, 30,000 µl/min, and 50,000 µl/min (the present embodiment).

The result of a simulation of the embodiment 1 is shown in FIG. 6 and Table 3.

A vertical axis of FIG. 6 represents a reaction amount in a unit area of the reaction field 4, and a horizontal axis represents a measuring time. The conditions of an effective antibody density of the reaction field 4 and an amount of an antibody in the specimen material solution 16 in the case of the present embodiment are set to be equivalent to those in the case of the comparative example.

(Conditions)

Measuring time: 1500 sec

Width of a flow passage: 1 mm

Height of a flow passage: 50 µm

Shape of a reaction field: 1 mm×2 mm

Amount of a specimen material solution: 100 µl

TABLE 3

| Flow rate (μl/min) | Amount of a specimen material solution (μl) | Effective antibody density (mol/cm$^2$) | Amount of an antigen (pg) | Number of passing (times/min) | Reaction amount in a unit area (pg/mm$^2$) | Note |
|---|---|---|---|---|---|---|
| 100 | 100 | 6.70 × 10$^{-12}$ | 0.0175 | 1 | 0.00164 | Comparative example |
| 300 | | | | 3 | 0.00187 | |
| 500 | | | | 5 | 0.00196 | |
| 1,000 | | | | 10 | 0.00223 | Embodiment |
| 5,000 | | | | 50 | 0.00229 | |
| 10,000 | | | | 100 | 0.00236 | |
| 30,000 | | | | 300 | 0.00244 | |
| 50,000 | | | | 500 | 0.00247 | |

Table 4 indicates a result of an actual measurement of the fluorescence intensity in the case in which a flow rate of the specimen material solution 16 is in a low flow rate region of 100 μl/min, 300 μl/min, and 500 μl/min (a comparative example) and is in a high flow rate region of 1,000 μl/min, 5,000 μl/min, 10,000 μl/min, 30,000 μl/min, and 50,000 μl/min (the present embodiment) for the SPFS apparatus that is provided with the microchip solution sending system 10 in which a width of the flow passage of the fine flow passage 2 is 1 mm and a height of the flow passage of the fine flow passage 2 is 50 μm.

TABLE 4

| Flow rate (μl/min) | Amount of a specimen material solution (μl) | Effective antibody density (mol/cm$^2$) | Amount of an antigen (pg) | Number of passing (times/min) | Fluorescence intensity | Note |
|---|---|---|---|---|---|---|
| 100 | 100 | 6.70 × 10$^{-12}$ | 0.0175 | 1 | 30,100 | Comparative example |
| 300 | | | | 3 | 34,200 | |
| 500 | | | | 5 | 35,900 | |
| 1,000 | | | | 10 | 40,800 | Embodiment |
| 5,000 | | | | 50 | 41,900 | |
| 10,000 | | | | 100 | 43,100 | |
| 30,000 | | | | 300 | 44,700 | |
| 50,000 | | | | 500 | 45,100 | |

As clarified by FIG. 6 and Table 3, at the point of time when a measuring time (1500 sec) elapses, as a rate of flow is higher, a reaction amount in a unit area is larger. A tendency of the simulation result can also be confirmed by a result of an actual measurement of the fluorescence intensity shown in Table 4.

As clarified by FIG. 6 and Table 3, a variation of a reaction amount that is associated with a variation of a rate of flow is smaller in the case of a high flow rate region (the present embodiment) as compared with the case of a low flow rate region (a comparative example). The tendency of the simulation result can also be confirmed by a result of an actual measurement of the fluorescence intensity shown in Table 4.

[Embodiment 2]

In the present embodiment, for the microchip solution sending system 10 described above, the reaction amount in a unit area was simulated in the case in which a width of the flow passage of the fine flow passage 2 is 3 mm, a height of the flow passage of the fine flow passage 2 is 500 μm, and a flow rate of the specimen material solution 16 is in a low flow rate region of 100 μl/min, 300 μl/min, and 500 μl/min (a comparative example) and is in a high flow rate region of 1,000 μl/min, 5,000 μl/min, 10,000 μl/min, 30,000 μl/min, and 50,000 μl/min (the present embodiment).

The result of a simulation of the embodiment 2 is shown in FIG. 8 and Table 5.

Figure 7:
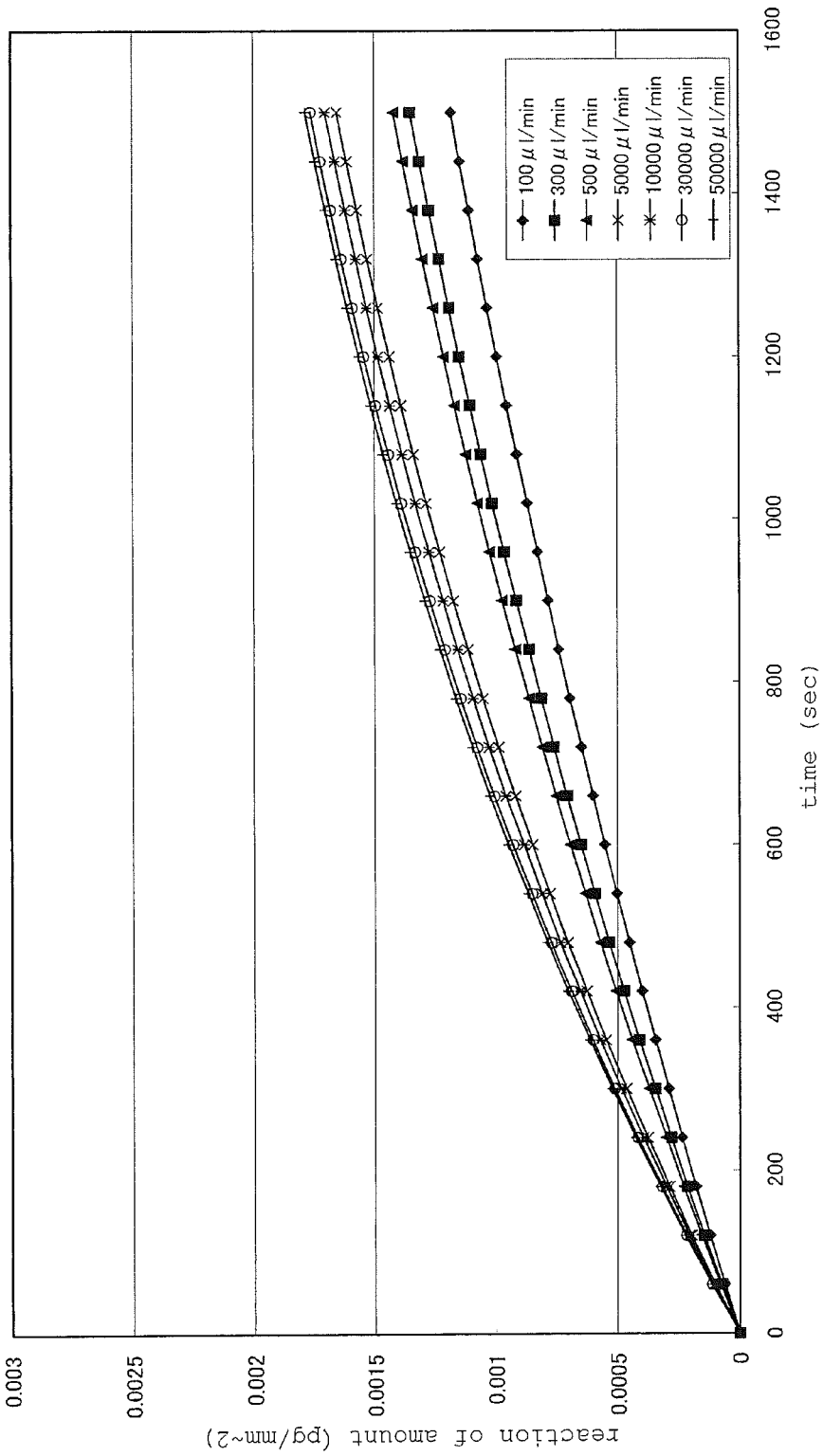
FIG. 7 is a graph that indicates a result of a simulation of the reaction amount in the case in which a flow rate of a specimen material solution is changed under the condition of the embodiment 2.

A vertical axis of FIG. 7 represents a reaction amount in a unit area of the reaction field 4, and a horizontal axis represents a measuring time. The conditions of an effective antibody density of the reaction field 4 and an amount of an antibody in the specimen material solution 16 in the case of the present embodiment are set to be equivalent to those in the case of the comparative example.

(Conditions)
Measuring time: 1500 sec
Width of a flow passage: 3 mm
Height of a flow passage: 500 μm
Shape of a reaction field: 3 mm×2 mm
Amount of a specimen material solution: 100 μl

TABLE 5

| Flow rate (μl/min) | Amount of a specimen material solution (μl) | Effective antibody density (mol/cm$^2$) | Amount of an antigen (pg) | Number of passing (times/min) | Fluorescence intensity | Note |
|---|---|---|---|---|---|---|
| 100 | 100 | 6.70 × 10$^{-12}$ | 0.0175 | 1 | 0.00118 | Comparative example |
| 300 | | | | 3 | 0.00135 | |
| 500 | | | | 5 | 0.00142 | |
| 1000 | | | | 10 | 0.00161 | Embodiment |
| 5,000 | | | | 50 | 0.00166 | |
| 10,000 | | | | 100 | 0.00170 | |
| 30,000 | | | | 300 | 0.00176 | |
| 50,000 | | | | 500 | 0.00179 | |

Table 6 indicates a result of an actual measurement of the fluorescence intensity in the case in which a flow rate of the specimen material solution 16 is in a low flow rate region of 100 μl/min, 300 μl/min, and 500 μl/min (a comparative example) and is in a high flow rate region of 1,000 μl/min, 5,000 μl/min, 10,000 μl/min, 30,000 μl/min, and 50,000 μl/min (the present embodiment) for the SPFS apparatus that is provided with the microchip solution sending system 10 in which a width of the flow passage of the fine flow passage 2 is 3 mm and a height of the flow passage of the fine flow passage 2 is 500 μm.

TABLE 6

| Flow rate (μl/min) | Amount of a specimen material solution (μl) | Effective antibody density (mol/cm$^2$) | Amount of an antigen (pg) | Number of passing (times/min) | Fluorescence intensity | Note |
|---|---|---|---|---|---|---|
| 100 | 100 | 6.70 × 10$^{-12}$ | 0.0175 | 1 | 21,600 | Comparative example |
| 300 | | | | 3 | 24,700 | |
| 500 | | | | 5 | 25,900 | |
| 1,000 | | | | 10 | 29,300 | Embodiment |
| 5,000 | | | | 50 | 30,300 | |
| 10,000 | | | | 100 | 31,200 | |
| 30,000 | | | | 300 | 32,300 | |
| 50,000 | | | | 500 | 32,700 | |

As clarified by FIG. 7 and Table 5, at the point of time when a measuring time (1500 sec) elapses, as a rate of flow is higher, a reaction amount in a unit area is larger. A tendency of the simulation result can also be confirmed by a result of an actual measurement of the fluorescence intensity shown in Table 6.

As clarified by FIG. 7 and Table 5, a variation of a reaction amount that is associated with a variation of a rate of flow is smaller in the case of a high flow rate region (the present embodiment) as compared with the case of a low flow rate region (a comparative example). The tendency of the simulation result can also be confirmed by a result of an actual measurement of the fluorescence intensity shown in Table 6.

[Embodiment 3]

A variation of a reaction amount that is associated with a variation of a rate of flow is decreased in the case in which a rate of flow of the specimen material solution is in the range of a high flow rate region. This will be described in detail in the following embodiment.

Tables 7 and 8 show a variation of a reaction amount with a variation coefficient CV value in the case in which a rate of flow is varied by ±10% to the predetermined rate of flow (μl/min). More specifically, for each of the three reaction fields 4 with difference shapes (1 mm×2 mm, 2 mm×2 mm, and 3 mm×2 mm), a CV value was obtained by a simulation in the case in which a rate of flow (μl/min) of the specimen material solution 16 is varied by ±10% from 50,000 μl/min, in the case in which a rate of flow (μl/min) of the specimen material solution 16 is varied by ±10% from 10,000 μl/min, in the case in which a rate of flow (μl/min) of the specimen material solution 16 is varied by ±10% from 1,000 μl/min, in the case in which a rate of flow (μl/min) of the specimen material solution 16 is varied by ±10% from 800 μl/min, and in the case in which a rate of flow (μl/min) of the specimen material solution 16 is varied by ±10% from 100 μl/min.

Table 7 indicates a result of a simulation in the case in which a measuring time (sec) is 600 seconds. Table 8 indicates a result of a simulation in the case in which a measuring time (sec) is 5400 seconds. The conditions of an amount of the specimen material solution 16, an effective antibody density and an amount of an antibody in the specimen material solution 16 and others are set to be equivalent to those in the case of the embodiment described above. A variation coefficient CV value (%) is obtained by dividing a standard deviation by an arithmetic mean value and indicates a relative dispersion.

TABLE 7

| Measuring time (sec) | Shape of a reaction field | Flow rate (μl/min) | CV value (%) | Note |
|---|---|---|---|---|
| 600 | 1 mm × 2 mm | 50,000 ± 10% | 0.27 | Embodiment |
| | | 10,000 ± 10% | 0.32 | |
| | | 1,000 ± 10% | 0.50 | |
| | | 800 ± 10% | 1.02 | Comparative example |
| | | 100 ± 10% | 1.45 | |
| | 2 mm × 2 mm | 50,000 ± 10% | 0.31 | Embodiment |
| | | 10,000 ± 10% | 0.33 | |
| | | 1,000 ± 10% | 0.56 | |
| | | 800 ± 10% | 1.20 | Comparative example |
| | | 100 ± 10% | 1.60 | |
| | 3 mm × 2 mm | 50,000 ± 10% | 0.32 | Embodiment |
| | | 10,000 ± 10% | 0.35 | |
| | | 1,000 ± 10% | 0.58 | |
| | | 800 ± 10% | 1.22 | Comparative example |
| | | 100 ± 10% | 1.67 | |

TABLE 8

| Measuring time (sec) | Shape of a reaction field | Flow rate (μl/min) | CV value (%) | Note |
|---|---|---|---|---|
| 5400 | 1 mm × 2 mm | 50,000 ± 10% | 0.12 | Embodiment |
| | | 10,000 ± 10% | 0.14 | |
| | | 1,000 ± 10% | 0.20 | |
| | | 800 ± 10% | 0.72 | Comparative example |
| | | 100 ± 10% | 0.91 | |
| | 2 mm × 2 mm | 50,000 ± 10% | 0.07 | Embodiment |
| | | 10,000 ± 10% | 0.10 | |
| | | 1,000 ± 10% | 0.12 | |
| | | 800 ± 10% | 0.68 | Comparative example |
| | | 100 ± 10% | 0.73 | |
| | 3 mm × 2 mm | 50,000 ± 10% | 0.03 | Embodiment |
| | | 10,000 ± 10% | 0.05 | |
| | | 1,000 ± 10% | 0.10 | |
| | | 800 ± 10% | 0.48 | Comparative example |
| | | 100 ± 10% | 0.56 | |

As clarified by Table 7 and Table 8, a CV value is smaller in the case of a high flow rate region (the present embodiment) as compared with the case of a low flow rate region (a comparative example). It is confirmed that a dispersion of a reaction amount can be suppressed for a high flow rate region as compared with a flow rate variation of the same level. This is similar in the case in which a measuring time (a reaction time) is shorter (Table 7) or longer (Table 8). In the case in which a measuring time (a reaction time) is longer, a dispersion of a reaction amount is smaller on the whole. This is because a saturation point is reached in the case in which a measuring time (a reaction time) is longer, whereby a dispersion of a reaction amount is smaller. Even in such a situation, it can be confirmed that an effect of suppressing a dispersion of a reaction amount is high by definition in a high flow rate region of 1,000 μl/min to 50,000 μl/min.

Although an amount of the specimen material solution, and an effective antibody density and an amount of an antibody in the specimen material solution have been described by using a certain example in the embodiment described in detail above, a similar tendency is indicated even in the case in which the values are varied.

REFERENCE SIGNS LIST

2: Fine flow passage
4: Reaction field
6: Inlet hole
8: Outlet hole
10: Microchip solution sending system
12: Outlet side flow passage
14: Solution sending pump
15: Control part
16: Specimen material solution
18: Specimen material solution container
20: Mixing part
22: Pipette
22a: End
22b: Base end part
30: Analyte
32: Antigen
100: Microchip solution sending system
102: Fine flow passage
104: Reaction field
106: Inlet hole
108: Outlet hole
110: Inlet side flow passage
112: Outlet side flow passage
114: Circulation solution sending pump
116: Specimen material solution
118: Specimen material solution container 200: Microchip solution sending system
202: Fine flow passage
204: Reaction field
206: Inlet hole
208: Outlet hole
210: Inlet side flow passage
212: Outlet side flow passage
214: Reciprocation solution sending pump
216: Specimen material solution
218: Specimen material solution container
gl: Air-liquid interface
ul: Height of the upper face of a flow passage of a fine flow passage
H: Height of the flow passage
v: Velocity of flow
l: Diffusion distance
L1: Length of a flow passage of a fine flow passage
D: Width of a flow passage of a fine flow passage
H: Height of a flow passage of a fine flow passage
L2: Length of a reaction field

What is claimed is:

1. A method of specimen material detection comprising providing a specimen material detection apparatus comprising a microchip solution sending system, the microchip solution sending system comprising:
   a flow passage that is provided with a reaction field to which an antibody that reacts with a specific antigen is fixed,
   a solution sending pump,
   a cross-section of the flow passage is in rectangular shape,
   a height of the flow passage is in the range of 50 μm to 500 μm, and
sending a specimen material solution that includes the specific antigen through the reaction field at a flow rate of 5,000 to 50,000 μl/min,
   wherein the step of sending the specimen material solution comprises sending the specimen material solution in a repetitive manner by repeating a reversal of a solution sending direction.

2. The method of claim 1, wherein the microchip solution sending system further comprises a mixing part that is connected to the flow passage in which the specimen material solution that has passed through the reaction field of the flow passage is stored temporarily and the specimen material solution that has been stored is stirred.

3. The method of claim 1, wherein:
   a width of the flow passage is in the range of 0.5 mm to 3 mm.

4. The method of claim 2, wherein:
   a width of the flow passage is in the range of 0.5 mm to 3 mm.

5. The method of claim 1, wherein the specimen material detection apparatus is a surface plasmon resonance apparatus (a SPR apparatus) or a surface plasmon field enhanced fluorescence spectroscopic measurement apparatus (a SPFS apparatus).

6. The method of claim 2, wherein the specimen material detection apparatus is a surface plasmon resonance apparatus (a SPR apparatus) or a surface plasmon field enhanced fluorescence spectroscopic measurement apparatus (a SPFS apparatus).

7. The method of claim 3, wherein the specimen material detection apparatus is a surface plasmon resonance apparatus (a SPR apparatus) or a surface plasmon field enhanced fluorescence spectroscopic measurement apparatus (a SPFS apparatus).

8. The method of claim 1, wherein a flow rate of the specimen material solution that is sent by the solution sending pump is in the range of 10,000 μl/min to 50,000 μl/min.

9. The method of claim 2, wherein a flow rate of the specimen material solution that is sent by the solution sending pump is in the range of 10,000 μl/min to 50,000 μl/min.

10. The method of claim 3, wherein a flow rate of the specimen material solution that is sent by the solution sending pump is in the range of 10,000 μl/min to 50,000 μl/min.

11. The method of claim 4, wherein a flow rate of the specimen material solution that is sent by the solution sending pump is in the range of 10,000 μl/min to 50,000 μl/min.

12. The method of claim 1, wherein the reaction field is disposed on an interior surface of the flow passage.

13. The method of claim 3, wherein the reaction field is disposed on an interior surface and is provided along an entire width of the interior surface.

14. The method of claim 1, wherein the reaction field is disposed on an interior surface of the flow passage and extends for a distance of approximately 2 mm in a length dimension of the flow passage.

* * * * *